(12) United States Patent
Berry et al.

(10) Patent No.: US 8,765,721 B2
(45) Date of Patent: Jul. 1, 2014

(54) COMPOSITION COMPRISING PHOSPHATIDYL SERINE AND AN ANTIGEN OR ALLERGEN AND THE USE THEREOF

(75) Inventors: Antony Rodney Berry, West Sussex (GB); Alan Worland Wheeler, West Sussex (GB)

(73) Assignee: Vaccine Technology Limited, Horsham, West Sussex (GB)

( * ) Notice: Subject to any disclaimer, the term of this patent is extended or adjusted under 35 U.S.C. 154(b) by 1384 days.

(21) Appl. No.: 11/720,284

(22) PCT Filed: Dec. 2, 2005

(86) PCT No.: PCT/GB2005/004656
§ 371 (c)(1),
(2), (4) Date: Sep. 3, 2007

(87) PCT Pub. No.: WO2006/059142
PCT Pub. Date: Jun. 8, 2006

(65) Prior Publication Data
US 2008/0107684 A1      May 8, 2008

(30) Foreign Application Priority Data
Dec. 2, 2004   (GB) .................................. 0426481.8

(51) Int. Cl.
*A61K 31/683*   (2006.01)

(52) U.S. Cl.
USPC ......................................................... 514/77

(58) Field of Classification Search
None
See application file for complete search history.

(56) References Cited

U.S. PATENT DOCUMENTS

| | | | |
|---|---|---|---|
| 6,511,677 B1 | 1/2003 | Brey et al. | |
| 6,953,591 B2 | 10/2005 | Bolton et al. | |

FOREIGN PATENT DOCUMENTS

| | | |
|---|---|---|
| EP | 0 356 340 A1 | 2/1990 |
| EP | 0 640 347 A1 | 3/1995 |
| JP | 09/012480 A | 1/1997 |
| JP | 63/309864 A | 12/1998 |
| WO | 93/17702 A1 | 9/1993 |
| WO | 99/33522 A3 | 7/1999 |
| WO | 99/33940 A1 | 7/1999 |
| WO | 02/24162 A1 | 3/2002 |

OTHER PUBLICATIONS

Brockman et al.; "Packing and Electrostatic Behavior of sn-2-Docosahexaenoyl and -Arachidonoyl Phosphoglycerides"; 2003; Biophysical Journal; 85: 2384-2396.*
Akoh et al.; "Composition of Mouse Peritoneal Macrophage Phospholipid Molecular Species"; 1990; Lipids; 25: 613-617.*
Parker et al.; "A Phosphatidylserine Species Inhibits a Range of TLR- but Not IL-1β-Induced Inflammatory Responses by Disruption of Membrane Microdomains"; 2008; The Journal of Immunology, 181: 5606-5617.*
Aramaki et al., Interferon-gamma Inductive Effect of Liposomes as an Immunoadjuvant, Vaccine 13(18):1809-1814 (1995).
Han et al., Application of Liposomes for Development of Oral Vaccines: Study of In Vitro Stability of Liposomes and Antibody Response to Antigen Associated with Liposomes after Oral Immunization, J. Vet. Med. Sci. 59(12):1109-1114 (1997).
Harding et al., Liposome-Encapsulated Antigens Engender Lysosomal Processing for Class II MHC Presentation and Cytosolic Processing for Class I Presentation, J. Immunology 147(9):2860-2863 (1991).
PCT Search Report from priority document PCT/GB2005/004656.
Patent Acts 1977: Search Report under Section 17(5) for GB0426481.8 (Mar. 23, 2005).
Fadok et al., "A Receptor for Phosphatidylserine Specific Clearance of Apoptotic Cells," Nature, vol. 405 (May 4, 2000).
Yabuuchi et al, "Positional Distribution of Fatty Acids in Glycerophosphatides of Bovine Gray Matter," Journal of Lipid Research, vol. 9 (1968).

* cited by examiner

*Primary Examiner* — Timothy Thomas
(74) *Attorney, Agent, or Firm* — Karen Canaan; CanaanLaw, P.C.

(57) ABSTRACT

Provided is a composition comprising a phosphatidyl serine receptor ligand for use in immune therapy. The composition may include an antigen or allergen together with the phosphatidyl serine receptor ligand. The compositions may be used for any type of immune therapy, such as immune modulation to an environmental antigen or allergen, down regulation of immune hypersensitivity reactions, and stimulation of antigen or allergen specific IgA and/or IgG4.

11 Claims, No Drawings

COMPOSITION COMPRISING PHOSPHATIDYL SERINE AND AN ANTIGEN OR ALLERGEN AND THE USE THEREOF

CROSS REFERENCE TO RELATED APPLICATIONS

This application claims priority under 35 U.S.C. §120 to PCT Application No. PCT/GB2005/004656, filed on Dec. 2, 2005, which claims priority to GB 0426481.8, filed on Dec. 2, 2004.

FIELD OF THE INVENTION

The present invention relates generally to compositions useful for immune therapy. More specifically, the present invention relates to compositions comprising a phosphatidyl serine receptor ligand, with or without an antigen or allergen, and methods of use in various immune therapies.

BACKGROUND OF THE INVENTION

The immune system has evolved specifically to detect and eliminate foreign or new material from a host. This material may be of viral, bacterial, or parasitic origin and may reside outside or within the cells of the host, or be of neoplastic origin.

The non-specific or innate immune system is usually the first line of defence to a new challenge. It comprises of barriers such as skin and mucous and specialist cells such as neutrophils and macrophages which are programmed to destroy foreign material by the secretion of enzymes or by engulfing it (phagocytosis). The innate immune system can be triggered by receptors on the surfaces of phagocytes (pattern receptors or Toll like receptors) which recognise general features of the foreign substances (PAMPS). At least 10 toll receptors are known, for example, TLR4 recognises lipopolysaccharides (LPS) from bacterial cell walls and TLR9 recognises the CpG DNA sequence. Phagocytes, when activated, release inflammatory cytokines which recruit cells involved with the primary specific immune response, such as T-cells. In addition many phagocytes can also act as antigen presenting cells (APC's) by internally processing foreign proteins and presenting fragments (epitopes) of them to the recruited specific cells of the acquired immune system as a prelude to the development of a specific immune response.

The specific immune response is generally either cell mediated, wherein killer T-cells destroy infected cells, or humoral, in which antibodies such as IgG bind to the foreign material and aid the process of destruction and removal from the body by the complement system and phagocytosis. In all cases, APCs present the epitopes to T-helper cells (Th) which, depending on the signalling cytokine profile from the APC and the T-helper cell type, produces a range of Th-cell responses. Th1 like responses are cell mediated and the T-cell secretes γ interferon as the primary cytokine. Th2 like responses are humoral and are mediated in part by the secreted cytokine interleukin 4. Activated Th2 cells help to activate resting B-cells ultimately resulting in antibody production. The specific immune response normally takes 10-14 days to develop.

In almost all primary specific immune responses acute inflammation is often found at the site of the lesion. IgG1 and IgE are known as inflammatory antibodies because they either activate the complement system or initiate the release of inflammatory cytokines from mast cells or basophils.

The complement system is a set of plasma proteins that act together to attack extracellular forms of pathogens. Complement results in the opsonization of pathogens, the recruitment of inflammatory cells and directs the killing of pathogens. The complement system can be activated by two different pathways: the classical complement pathway and the alternative complement pathway. The classical pathway is antibody-dependent and is activated by the binding of antibody molecules (specifically IgM and IgG1, IgG2, and IgG3) to a foreign particle. The role of complement in inflammation and tissue injury has become apparent through clinical investigations and discoveries that the pathogenesis of certain experimental inflammatory diseases is complement-dependent.

Mast cells, located in perivascular connective tissue throughout the body, are involved in Type I allergic disease. Type I Allergic disease is a disease of the developed world which affects up to 30% of the population of the USA and Europe. IgE mediated allergy is also implicated in asthma and over 70% of asthmatics are allergic to one or more allergen. The cost of allergic disease probably exceeds $10 billion in the USA alone. When inhaled or trapped on mucosal surfaces, pollens release proteins (allergens) which, in some individuals, results in an acute inflammatory response mediated by allergen specific IgE antibodies bound to mast cells. The allergic reaction is triggered when the allergens cross-link preformed IgE, bound to mast cells, resulting in de-granulation of the mast cell and the release of copious amount of inflammatory mediators including histamine. In severe cases allergic disease can result in asthma and anaphylaxis, a life threatening condition.

In contrast to the initiation of the immune response, much less is known about the resolution of inflammation following an antigen or allergen challenge. It is thought that another class of T-cell is involved, the so called regulatory T-cell or T-reg. These cells under the influence of anti-inflammatory cytokines TNFβ and interleukin 10, which are involved in dampening down the T-cell responses, switch the antibody responses to IgA and IgG4 both of which are non-inflammatory antibodies and do not activate the complement system. Secretory IgA (sIgA) is found on mucous membranes and has been shown to neutralize viruses and prevent their adherence to the epithelial cells lining the mucous. McCluskie et al., MICROBES INFECT. 1(9):685-98 (1999); Ogra et al., CLIN MICROBIOL REV. 14(2):430-45 (2001); Rosenthal et al., SEMIN IMMUNOL. 9(5):303-14 (1997); van Ginkel et al., EMERG INFECT DIS. 6(2):123-32 (2000).

Recent studies on the mechanism of removal of inflammatory cells such as neutrophils from the site of an inflammatory lesion have focused on the rapid turnover and apoptosis of these cells. Neutrophils are phagocytes and, after they have engulfed foreign material, a safe and effective way of their disposal is needed. Macrophages, having engulfed a dying neutrophil, undergo significant changes which alter their pattern of cytokine secretion (Fadok et al, J. CLIN. INVEST. 101: 890-898 (1998)), switching production from inflammatory cytokine to anti-inflammatory cytokine synthesis which include, among others, TGFβ.

It has recently been shown that phosphatidylserine may be a general recognition marker for the removal of apoptotic cells, such as neutrophils, by phagocytes (Fadok et al., NATURE 405:85-90 (2000)), while U.S. Pat. No. 6,953,591 to Belyaysky et al. discloses the use of phosphatidylserine for treating T-cell-mediated diseases.

SUMMARY OF THE INVENTION

Formulations are provided which modulate an immune response. In particular, formulations are provided which may down regulate immune hypersensitivity reactions and may stimulate antigen or allergen specific IgA and/or IgG4 to provide protection against the invasion of infective agents or allergic substances systematically or via mucosal surfaces, respectively.

Formulations are provided which comprise a phosphatidyl serine receptor ligand. Such formulations may modulate an immune response to an environmental antigen/allergen. The phosphatidyl serine receptor ligand may be administered prior to, simultaneously, or after encounter with the antigen/allergen.

Formulations are also provided which comprise both a phosphatidyl serine receptor ligand and an antigen or allergen.

According to one aspect of the present invention there is provided a composition comprising a phosphatidyl serine receptor ligand herein defined.

According to another aspect of the present invention there is provided a composition comprising:
(i) an antigen; and
(ii) a phosphatidyl serine receptor ligand.

According to another aspect of the present invention there is provided a composition comprising:
(i) an allergen; and
(ii) a phosphatidyl serine receptor ligand.

In one embodiment the ligand used in the present invention has the structure of formula (I):

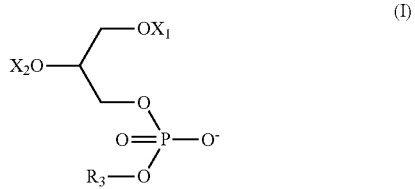

(I)

wherein $X_1$ is selected from H or

wherein $X_2$ is selected from H or wherein "*" represents the point of attachment to the remainder of the molecule; and wherein the $R_1$ and $R_2$ moieties are independently selected from hydrogen, alkyl, or an alkenyl group, each of which may be optionally mono- or poly-substituted with a group selected from halogeno, $NO_2$, CN, $(CH_2)_m OR^a$, where m is 0, 1, 2, or 3, $O(CH_2)_n OR^b$, where n is 1, 2, or 3, $NR^c R^d$, $CF_3$, $COOR^e$, $CONR^f R^g$, $COR^h$, $SO_3H$, $SO_2R^i$, $SO_2NR^j R^k$, cycloalkyl, alkenyl or aryl; and $R^{a-k}$ are each independently H or alkyl; and wherein $R_3$ is an alkyl, alkenyl, cycloalkyl, or aryl group, each of which may be optionally mono- or poly-substituted with a group selected from halogen, haloalkyl, $NO_2$, CN, $(CH_2)_m OR^a$, where m is 0, 1, 2 or 3, $O(CH_2)_n OR^b$, where n is 1, 2, or 3, $NR^c R^d$, $CF_3$, $COOR^e$, $CONR^f R^g$, $COR^h$, $SO_3H$, $SO_2R^i$, $SO_2NR^j R^k$, cycloalkyl, alkenyl or aryl; and $R^{a-k}$ are each independently H or alkyl; and wherein $R_3$ comprises at least one atom that has a greater electronegativity than carbon.

In one aspect of the present invention $R_1$ and $R_2$ are independently selected from hydrogen, alkyl or an alkenyl group and $R_3$ is a polar group.

Preferably $R_3$ comprises at least one atom that has a greater electronegativity than carbon.

In one embodiment $R_1$ and/or $R_2$ is mono- or poly-substituted with a $C_1$-$C_6$ alkoxy, hydroxyl, amino and/or a halogeno group.

In another embodiment $R_3$ is mono- or poly-substituted with a hyroxyl, carboxyl, carboxylate, NR'R" wherein R' and R" are independently selected form H or $C_1$-$C_6$ alkyl, $C_1$-$C_6$ alkoxy, $C_1$-$C_6$ alkyl optionally substituted with hydroxyl or carboxyl, $C(O)NH_2$, $CF_3$ or a $C_1$-$C_6$ alkyl-COOH group.

Preferably $R_3$ is mono- or poly-substituted with a carboxy, hydroxy and/or amino group.

Preferably $R_1$ and/or $R_2$ and/or $R_3$ is optionally substituted with 1 to 3 groups.

In one embodiment $R_1$ and/or $R_2$ is an unbranched alkyl or alkenyl group.

$R_1$ and or $R_2$ may be an alkyl or alkenyl group that additionally contains 1 or more, preferably 1 to 3, heteroatoms independently selected from N, O, or S.

In another embodiment $R_2$ is an unbranched alkyl or alkenyl group.

$R_1$ and $R_2$ may independently comprise 1 to 60, more preferably 1 to 26, more preferably 14 to 26, more preferably 16 to 22, more preferably 18 to 22 carbon atoms.

In one embodiment $R_1$ is an alkenyl group comprising 1 to 6 double bonds.

In another embodiment $R_1$ is an alkenyl group comprising 1 to 4 double bonds.

In another embodiment $R_1$ is an alkenyl group comprising 1 double bond.

In another embodiment $R_2$ is an alkenyl group comprising 1 to 6 double bonds.

In another embodiment $R_2$ is an alkenyl group comprising 1 to 4 double bonds.

In another embodiment $R_2$ is an alkenyl group comprising 4 double bonds.

In another embodiment $R_2$ is an alkenyl group comprising 1 double bond.

In one embodiment $X_1$ and $X_2$ are each, independently selected from hydrogen and a saturated or unsaturated fatty acid acyl group or a derivative or salt thereof.

Examples of fatty acid acyl groups are hexanoyl, caproyl, auroyl, phytanoyl, heptadecanoyl, linoleoyl, erucoyl, docosahexanenoyl, heptanoyl, octanoyl, nonanoyl, decanoyl, undecanoyl, lauroyl, tridecanoyl, myristoyl, pentadecanoyl, palmitoyl, heptadecanoyl, stearoyl, oleoyl, nonadecanoyl, arachidoyl, behenoyl and lignoceroyl.

In one embodiment $X_1$ is selected from a stearoyl group or a derivative or salt thereof, an oleoyl group or a derivative or salt thereof and hydrogen.

In one embodiment $X_2$ is selected from an arachidonoyl, or a derivative or salt thereof, an oleoyl group or a derivative or salt thereof, or hydrogen.

$R_3$ may comprise 1 to 8, 1 to 6, 1 to 3 or 1 atom that has a greater electronegativity than carbon.

Preferably the atom that has a greater electronegativity than carbon is selected from the group comprising O N, S or halogen. More preferably the atom that has a greater electronegativity than carbon is selected from the group comprising O or N.

In one embodiment R$_3$ comprises an alkyl group.

In another embodiment R$_3$ comprises a cycloalkyl group.

In another embodiment R$_3$ comprises an aryl group.

Preferably R$_3$ comprises 1 to 15, 1 to 12, 3 to 9, 2 to 8 or 3 to 6 carbon atoms.

In another embodiment R$_3$ is selected from the group consisting of:

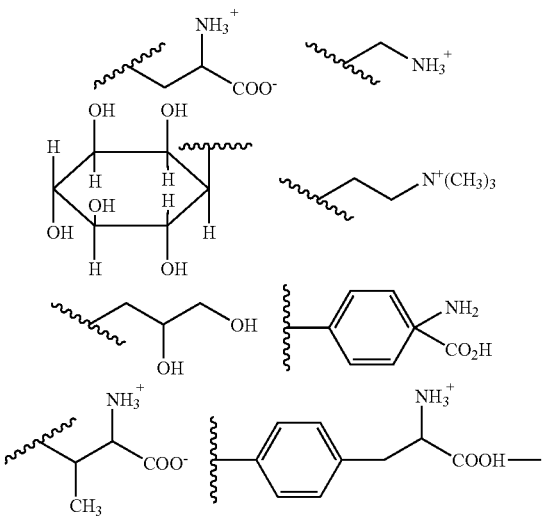

and derivatives thereof.

R$_3$ may be an amino acid or a derivative thereof. Preferably the amino acid is a natural amino acid. Preferably the phosphorous oxygen is attached to the carbon of the amino acid.

In one embodiment R$_3$ is

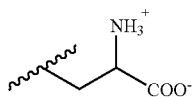

or a derivative thereof.

In one embodiment the phosphatidyl serine receptor ligand is phosphatidyl serine or a derivative or salt thereof.

In another embodiment the ligand is selected from the group consisting of di-oleoyl phosphatidyl serine, lyso-oleoyl phosphatidyl serine and stearoyl-arachidonoyl phosphatidyl serine.

The antigen or allergen used in the present invention may be derived from a bacterium, virus, or neoplasm.

The antigen or allergen may be in the form of a polypeptide, or a vector comprising a polynucleotide encoding an antigenic polypeptide and operably linked to a regulatory sequence permitting expression of the polynucleotide.

According to another aspect of the present invention there is provided a composition comprising a phosphatidyl serine receptor ligand herein defined. Such a composition may comprise no antigen or allergen. In one embodiment, such a composition does not comprise a pharmaceutically effective amount of an antigen or allergen.

The compositions of the present invention preferably comprise a pharmaceutically effective amount of phosphatidyl serine receptor ligand, and/or antigen or allergen.

The composition of the present invention may comprise an adjuvant. Suitable adjuvants include, for example, mono-phosphoryl lipid A and its derivatives and analogues and the CpG DNA motif and its derivatives and analogues.

Preferably, the composition of the present invention comprises a pharmaceutically acceptable carrier, diluent, or excipient.

According to another aspect of the present invention there is provided a composition of the present invention in the form of a vaccine. The vaccine may be a prophylactic vaccine or a therapeutic vaccine.

The composition of the present invention may be a non-oral composition i.e., a composition that is not swallowed by the recipient.

In one embodiment, the phosphatidyl serine receptor ligand is present in a composition to provide a dosage in the range of 5-500 µg.

In another embodiment, the phosphatidyl serine receptor ligand is present in a composition to provide a dosage in the range of 10-100 µg.

In another embodiment, the phosphatidyl serine receptor ligand is present in a composition to provide a dosage in the range of 10-50 µg.

According to another aspect of the present invention there is provided a composition of the present invention for use in medicine.

According to another aspect of the present invention there is provided products containing an allergen or an antigen and a phosphatidyl serine receptor ligand of the present invention as a combined preparation for simultaneous, separate or sequential use in medicine.

In one embodiment the antigen or allergen and phosphatidyl serine receptor ligand are administered simultaneously.

In another embodiment the antigen or allergen and phosphatidyl serine receptor ligand are administered sequentially. The phosphitdyl serine receptor ligand may be administered prior to the antigen or allergen or after.

In another embodiment the antigen or allergen and phosphatidyl serine receptor ligand are administered subcutaneously.

In another embodiment the phosphatidyl serine receptor ligand and/or allergen may be administered to an organ which is exposed to a high natural allergen challenge, such as, but not limited to, the skin, nose or mouth.

According to another aspect of the present invention there is provided use of a composition or a product of the present invention for the preparation of a medicament for modulating an immune response.

According to another aspect of the present invention there is provided a method of modulating an immune response in a subject comprising administering a composition or a product of the present invention to the subject.

According to another aspect of the present invention there is provided use of a composition or a product of the present invention for the preparation of a medicament for treating, or preventing, or reducing the susceptibility to, bacterial or viral infection or cancer.

According to another aspect of the present invention there is provided a method of treating, or preventing, or reducing the susceptibility to, bacterial or viral infection, or cancer, in a subject comprising administering a composition or product of the present invention to the subject.

According to another aspect of the present invention there is provided use of a composition or a product of the present invention for the manufacture of a medicament for treating or preventing an allergic reaction.

According to another aspect of the present invention there is provided a method of treating, or preventing, or reducing the susceptibility of an allergic reaction comprising administering a composition or product of the present invention to a subject.

According to another aspect of the present invention there is provided use of a composition or a product of the present invention for the manufacture of a medicament for treating or preventing an immune hypersensitivity reaction, preferably type 1-4, more preferably type 1 or 4, more preferably type 1.

According to another aspect of the present invention there is provided a method of treating, or preventing, or reducing the susceptibility of an immune hypersensitivity reaction comprising administering a composition or product of the present invention to a subject.

Preferably the immune hypersensitivity reaction is a pre-existing disorder i.e., a disorder that the subject suffers or has suffered from.

Preferably the immune hypersensitivity reaction is a Type 1 hypersensitivity reaction.

According to another aspect of the present invention there is provided use of a composition of the present invention comprising a phosphatidyl serine receptor ligand and an antigen or allergen, or a product of the present invention for the manufacture of a medicament for raising an anti-inflammatory immune response to said antigen or allergen.

According to another aspect of the present invention there is provided use of a composition comprising a phosphatidyl serine receptor ligand for the manufacture of a medicament for raising an anti-inflammatory immune response to an antigen or allergen.

According to another aspect of the present invention there is provided a method of raising an anti-inflammatory immune response in a subject comprising administering a composition comprising a phosphatidyl serine receptor ligand and an antigen or allergen, or product of the present invention to a subject.

According to another aspect of the present invention there is provided a method of raising an anti-inflammatory immune response in a subject comprising administering a composition comprising a phosphatidyl serine receptor ligand to a subject prior to, simultaneously or after exposure of the subject to an antigen or allergen.

Preferably the anti-inflammatory immune response involves an anti-inflammatory antibody response wherein the antibodies include those that do not activate complement.

In one embodiment the antibodies raised in the anti-inflammatory antibody response include IgA and/or IgG4.

According to another aspect of the present invention there is provided use of a composition comprising a phosphatidyl serine receptor ligand and an antigen or allergen, or a product of the present invention for the manufacture of a medicament for reducing the levels of inflammatory antibodies in an immune response to the antigen or allergen.

According to another aspect of the present invention there is provided a method of reducing the levels of inflammatory antibodies in an immune response to an antigen or allergen in a subject comprising administering a composition comprising a phosphatidyl serine receptor ligand and an antigen or allergen, or product of the present invention to a subject.

According to another aspect of the present invention there is provided use of a composition comprising a phosphatidyl serine receptor ligand for the manufacture of a medicament for reducing the levels of inflammatory antibodies in an immune response to an antigen or allergen.

According to another aspect of the present invention there is provided a method of reducing the levels of inflammatory antibodies in an immune response to an antigen or allergen in a subject comprising administering a composition comprising a phosphatidyl serine receptor ligand to a subject prior to, simultaneously or after exposure of the subject to an antigen or allergen.

According to another aspect of the present invention there is provided use of a composition or a product of the present invention for the manufacture of a medicament for inducing an immune response which is associated with reduced levels of inflammatory antibodies. In one embodiment the inflammatory antibodies are those that activate complement.

In one embodiment the inflammatory antibodies are IgE or IgG 1, or both.

According to another aspect of the present invention there is provided use of a composition or a product of the present invention for the manufacture of a medicament for treating or preventing autoimmune disease.

According to another aspect of the present invention there is provided a method of raising an anti-inflammatory immune response in a subject comprising administering a composition or product of the present invention to a subject.

According to another aspect of the present invention there is provided use of a composition or a product of the present invention in a method for producing antibodies which recognise the antigen or allergen of the composition.

Preferably the antibodies are selected from IgA and IgG4.

According to another aspect of the present invention there is provided use of an antibody produced according to the above method for the preparation of a medicament for treating or preventing a bacterial or viral infection, cancer or an immune hypersensitivity reaction.

DETAILED DESCRIPTION OF THE INVENTION

Antigen

The term "antigen" is used to indicate any molecule that can be specifically recognised by the adaptive elements of the immune response, i.e. by B cells or T cells, or both.

The antigen used in the present invention is preferably an immunogen, i.e. an antigen which activates immune cells to generate an immune response against itself. The antigen may be obtained by recombinant means or peptide synthesis, or from natural sources or extracts and may be derived from any living or non-living organisms.

The antigen may be derived from bacteria, such as, for example anthrax, *campylobacter*, cholera, diphtheria, enterotoxigenic *E. coli, giardia*, gonococcus, *Helicobacter pylori, Hemophilus influenza* B, *Hemophilus influenza* non-typable, meningococcus, pertussis, pneumococcus, *salmonella, shigella, Streptococcus* B, group A *Streptococcus*, tetanus, *Vibrio cholerae, Yersinia, Staphylococcus, Pseudomonas* species and *Clostridia* species.

The antigen may be derived from viruses, such as, for example adenovirus, dengue serotypes 1 to 4, ebola (Jahrling et al., ARCH VIROL SUPPL, 11:135-140, (1996)), enterovirus, hepatitis serotypes A to E (Blum, DIGESTION 56:85-95 (1995); Katkov, MED CLIN NORTH AM 80:189-200 (1996); Lieberman and Greenberg, ADV PEDIATR INFECT DIS 11:333-363 (1996); Mast et al., ANNU REV MED 47:257-266 (1996)), herpes simplex virus 1 or 2, human immunodeficiency virus (Deprez et al., VACCINE 14:375-382 (1996)), influenza, Japanese equine encephalitis, measles, Norwalk, papilloma virus, parvovirus B19, polio, rabies, rotavirus, rubella, rubeola, vaccinia, vaccinia constructs containing genes coding for other antigens such as malaria antigens, varicella, and yellow fever. Parasites include, for example: *Entamoeba histolytica* (Zhang et al., INFECT IMMUN 63:1349-1355); *Plasmodium* (Bathurst et al., VACCINE 11:449-456 (1993)), Toxoplasmosis, and the Helminths.

A multivalent antigen formulation may be used to induce an immune response to more than one antigen at the same time. Conjugates may be used to induce an immune response to multiple antigens, to boost the immune response, or both.

Allergen

The term "allergen" is used to describe an antigen that elicits an unwanted immune hypersensitivity or allergic reaction.

An allergy is a hypersensitivity response to an environmental antigen (allergen).

The allergen used in the present invention may be derived from any allergy causing substance, such as, but not limited, to pollen (e.g. ragweed or birch pollen), food, insect venom, mould and animal derived material such as animal fur or mites such as house dusts (e.g., *D. farinae* or *D. pteronyssinus*).

The antigen or allergen may be chemically modified by reaction with known substances, for example, but not limited to formaldehyde or glutaraldehyde, which retain or enhance the desired immunogenic properties of the antigen whilst helping to avoid unwanted adverse effects. Such modifications are known in the art. An example of a modified antigen is tetanus toxoid derived from tetanus toxin by reaction with formaldehyde.

Immune Hypersensitivity

As herein defined, immune hypersensitivity means a state of altered reactivity in which the body reacts with an exaggerated immune response to a foreign substance (allergen). There are four types of hypersensitivity reaction (Types I, II, III and IV). The first three are antibody-mediated; the fourth is mediated mainly by T cells and macrophages.

Type I, anaphylactic or immediate-type hypersensitivity is an allergic reaction provoked by re-exposure to an allergen. Exposure may be by ingestion, inhalation, injection or direct contact. The reaction is mediated by IgE antibodies and produced by the immediate release of histamine, arachidonate and derivatives by basophils and mast cells. This causes an inflammatory response leading to an immediate (seconds to minutes) reaction which may be followed by a late phase response or reaction, causing, for example, asthma, hay fever, systematic anaphylaxis or contact dermatitis.

Phosphatidyl Serine Receptor Ligand

The composition of the present invention comprises a ligand capable of binding, preferably selectively, to a phosphatidyl serine receptor. Preferably the ligands are recognised by the phosphatidyl serine receptor on the surface of phagocytes or endocytes, thereby up-regulating cytokine production.

Phosphatidyl serines, as part of their function in signalling apoptosis, are recognized by a receptor on phagocytic cells which maybe a specific receptor co-located with CD14 or part of the CD14 complex and subsequently may down regulate the phagocyte via presentation to toll like receptors such as TLR2 and TLR4. Phosphatidyl serine receptor ligands may prevent the expression of inflammatory cytokines by phagocytic cells resulting from activation by lipo-polysaccharide derived from bacteria or prevent pro-inflammatory cytokines activating smooth muscle cells found in human airways.

The term phosphatidyl serine receptor refers to a receptor present on the surface of phagocytes and endocytes that recognises phosphatidyl serine (Fadok, V. A. et al. Nature 405, 85-90 (2000)).

Assays for screening for such ligands may employ a phosphatidyl serine receptor which may be free in solution, affixed to a solid support, borne on a cell surface, or located intracellularly, wherein the formation of complexes between the receptor and the target may be measured by appropriately adapting methods well known in the art.

Phosphatidyl serine receptor ligands may be screened by measuring their ability to reduce ear swelling in the murine contact hypersensitivity (CHS) model (see, for example, U.S. patent application Ser. No. 09/957,698 (publication number US 2002/0086049)), a model accepted in the art. Mouse ears are challenged with, for example, 2,4-dinitrofluorobenzene (DNFB), and the extent of ear swelling is used as a measure of the CHS response. The ability of the phosphatidyl serine receptor ligand to reduce the ear swelling can be assessed by comparing the ear swelling in mice injected with the ligand with mice that have not been injected with the ligand. The ligands used in the present invention are preferably those that reduce ear swelling in the CHS model.

Phosphatidyl serine receptor ligands may also be screened by measuring their ability to inhibit the phagocytosis of apoptotic cells, as described in Fadok et al., Nature 405:85-90, 2000. The ligands used in the present invention are preferably those that are capable of inhibiting the phagocytosis of apoptotic cells.

In one embodiment the ligand is a phosphatidyl serine. The phosphatidyl serine may be from any natural or commercial source. Phosphatidylserine molecules may be synthesised using synthetic methods well known to those skilled in the art. Phosphatidylserine synthesis is described in, for example Morgans D, Bioorganic Med Chem Letts 4(6): 827 (1994); Roodsari, F S, J Org Chem 64(21): 7727-7737 (1999); Diaz et al., Bioconjugate Chemistry 9(2): 250-254 1998; Infante M R. Frontiers in Colloid Chemistry 123/124: 49-70 (1997); Lindberg J, J Org Chem 67; part 1:194-199 (2002); Comfurius et al., Biochem Biophys Acta 488:36-42 (1977); Na et al., JAOCS 67:776-770 (1990); Yaqoah et al., Process Biochemistry 36 (12):1181-1185 (2001); Duclos et al., Chem Phys Lipids 66(3): 161-170 (1993); Turner et al., Journal OF Lipid Research 5:616-622 (1964); Vares et al., J Org Chem 68(26):10073-8 (2003); Ebli et al., Chem Phys Lipids 26(4):405-29 (1980); Rosenthal et al., Methods Enzymol 35:429-529 (1975); Braksmayer et al., Chem Phys Lipids 19(2):93-98 (1977); Morillo et al., Lipids 31(5):541-6 (1996); Nicholas et al., Lipids 18(6):434-8 (1983); Aneja et al., Biochim Biophys Acta 218(1):102-11 (1970); Lindberg et al., J Org Chem 67(1): 194-9 (2002); Radhakrishnan et al., Methods Enzymol. 72:408-33 (1981); Moore et al. Tetrahedron Lett. 50:4423-6 (1970).

Phosphatidylserine is made up of a glycerophosphate skeleton linked to two fatty acid molecules and the amino acid L-serine. In nature the exact composition of the fatty acids varies depending on the source of the phosphatidylserine. For example, in human plasma, 1-stearoyl-2-oleoyl (see structure below) and 1-stearoyl-2-arachidonoyl species predominate, but in brain and many other tissues 1-stearoyl-2-docosahexaenoyl species are very abundant.

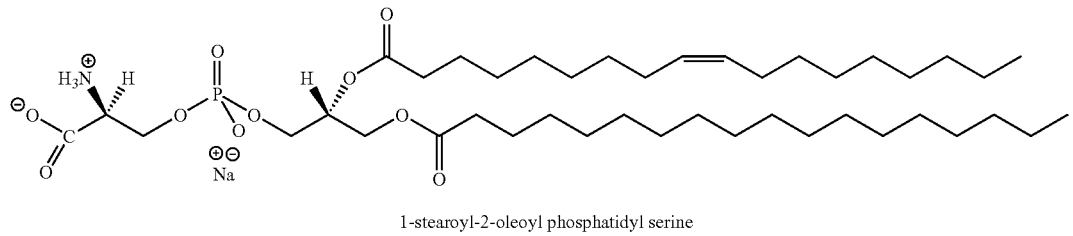

1-stearoyl-2-oleoyl phosphatidyl serine

Examples of ligands for use in the present invention include di-oleoyl phosphatidyl serine, lyso-oleoyl phosphatidyl serine, di-stearoyl phosphatidyl serine, lyso-stearoyl phosphatidyl serine and steroyl-arachidonyl phosphatidyl serine.

The phospholipase A (PLA2) superfamily represents a heterogeneous group of enzymes with key roles in inflammation whose common feature is to hydrolyse the fatty acid present at the sn-2 position of phospholipids.

PLA2 plays a key role in cellular signalling by generating a wide array of biologically active lipid mediators. PLA2-mediated hydrolysis of phospholipids generates the release of arachidonic acid which may serve as a substrate for the generation of other lipid messengers such as prostaglandins, which can then go on to generate an inflammatory response.

In one embodiment of the present invention, an arachidonoyl group is present at position $X_1$ or $X_2$ of the ligand. When this is the case, the arachidonic acid may be released from the ligand under the influence of PLA2, stimulating an inflammatory response. The residual lyso phosphatidyl serine receptor ligand may then serve to modulate the non-inflammatory response.

Thus, the ligand of the present invention can be used to modulate the immune response either up or down depending on the nature of the $X_2$ functional group in combination with the residual lyso phosphatidyl group produced by the action of PLA2.

As used herein, the term "alkyl" includes both saturated straight chain and branched alkyl groups.

As used herein, the term "alkenyl" refers to a group containing one or more carbon-carbon double bonds, which may be branched or unbranched.

As used herein, the term "aryl" refers to a mono- or multi-ringed aromatic group. Preferably the multi-ringed aromatic group is bi- or tri-ringed.

As used herein, the term "cycloalkyl" refers to a mono- or multi-ringed cyclic alkyl. Preferably the multi-ringed cyclic alkyl group is bi- or tri-ringed.

Preferably, the phosphatidyl serine receptor ligand is phosphatidyl serine or a derivative salt thereof. The term "derivative" is used to mean a phosphatidyl serine receptor ligand which retains the activity of phosphatidyl serine.

Examples of phosphatidyl serine receptor ligands include di-oleoyl-phosphatidyl serine and lyso-oleoyl-phosphatidyl serine.

The phosphatidyl serine receptor ligand used in the present invention may be in the form of a liposome.

The phosphatidyl serine receptor ligand may be carried by a liposome or included in a liposome.

The phosphatidyl serine receptor ligand used in the present invention may comprise part of a liposome. In other words, the phosphatidyl serine receptor ligand can form the membrane of a liposome, either as the sole constituent of the membrane or as a major or minor component thereof, with other phospholipids and/or membrane forming materials. The liposome may be used as a carrier for the 'active phosphatidyl serine receptor ligand' wherein said active ligand forms part of the surface of the liposome.

The phosphatidyl serine receptor may be chemically attached by chemical modification to a liposome surface. Methods of preparing liposomes are well known in the art (see, for example, New, R. C., "Liposomes: A Practical Approach," IRL Press at Oxford University Press, Oxford, England (1990)).

In one embodiment, the phosphatidyl serine receptor ligand used in the present invention is not in the form of a liposome. By the term 'liposome', it is meant an artificial microscopic vesicle consisting of an aqueous core enclosed in one or more phospholipid layers.

Preferably the phosphatidyl serine receptor ligand is an active ingredient in the compositions of the present invention. That is to say the ligand stimulates changes in immune or antibody response.

Antibodies

It will be appreciated that the nature and nomenclature of antibodies differs between species. The antibodies referred to herein refer to the human antibody and the counterpart antibodies found in other mammals and animals. The counterpart antibodies are based on similarities in biological and functional activities. For example, the murine counterparts of human IgE and human IgA are murine IgE and murine IgA respectively. On the other hand, human IgG4 is known not to activate complement and is considered to be most similar to murine IgG1.

Murine IgG2a and IgG2b and human IgG1 and IgG3 share the ability to fix complement and bind to protein antigens (M. G. Scott, D. E. Briles, and M. H. Nahm. SELECTIVE IgG SUBCLASS EXPRESSION: BIOLOGIC, CLINICAL AND FUNCTIONAL ASPECTS, p. 161-183, 1990).

Preparation

The compositions of the invention may be administered directly. Preferably the composition is combined with a pharmaceutically acceptable carrier, excipient or diluent to produce a pharmaceutical composition.

Treatment

It is to be appreciated that all references herein to treatment include curative, palliative and prophylactic treatment. The treatment of mammals is particularly preferred. Both human and veterinary treatments are within the scope of the present invention. As used herein, the term "subject" is meant to include human and animal subjects.

Pharmaceutical Compositions

A pharmaceutical composition is a composition that comprises or consists of a therapeutically effective amount of a pharmaceutically active agent. It preferably includes a pharmaceutically acceptable carrier, diluent, or excipients (including combinations thereof). Acceptable carriers or diluents for therapeutic use are well known in the pharmaceutical art, and are described, for example, in REMINGTON'S PHARMACEUTICAL SCIENCES, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously, or sublingually. For parenteral administration, the compositions may be best used in the form of a sterile aqueous solution which may contain other substances, for example enough salts or monosaccharides to make the solution isotonic with blood. For buccal or sublingual administration the compositions may be administered in the form of, for example, drops, sprays, creams, gels, tablets or lozenges which can be formulated in a conventional manner.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

In one embodiment, the composition of the present invention is a non-oral composition. That is, the composition is not swallowed by the recipient.

In one aspect of the present invention, compositions are provided which comprise a phosphatidyl serine receptor ligand. Such compositions may modulate an immune response to an environmental antigen/allergen. In one embodiment, the composition comprising the phosphatidyl serine receptor ligand may be administered prior to, simultaneously or after encounter with the antigen/allergen. Thus, the source of the antigen or allergen may be the environment of the subject.

Compositions are also provided which comprise both a phosphatidyl serine receptor ligand and an antigen or allergen.

Products

Products of the invention may contain antigen or allergen, preferably an allergen, and a phosphatidyl serine receptor ligand. The antigen or allergen and phosphatidyl serine receptor ligand may be present as separate compositions and may be administered simultaneously, separately or sequentially for use in treating an unwanted immune hypersensitivity reaction.

If the antigen or allergen and phosphatidyl serine receptor ligand are administered separately or sequentially, it is preferable that the method of administration allows the allergen and phosphatidyl serine receptor ligand to encounter the same target cells. This may be achieved by, for example, subcutaneous injection.

The pharmaceutical composition of the present invention may comprise the triple combination of monophosphoryl lipid A (MPL), antigen, and phosphatidyl serine receptor ligand.

Vaccines

The preparation of vaccines which contain an immunogenic polypeptide(s)/polynucleotide(s) as active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine.

An adjuvant is any pharmacologically acceptable substance which enhances the immune response to an antigen or allergen. Thus a Th1-inducing adjuvant enhances the response of Th1 cells to an antigen or allergen.

Examples of adjuvants which may be effective include but are not limited to: aluminum hydroxide, tyrosine and derivatives thereof N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminum hydroxide), or a mixture of Amphigen and Alhydrogel, tyrosine and derivatives thereof and calcium phosphate are used.

Preferred adjuvants are those known to interact with toll like receptors on phagocytic and endocyte and/or antigen presenting cells, for example, but not limited to toll like receptors 2 and or 4 and or 9. Example of these adjuvants are, but not limited to, the Th1 inducing adjuvant monophosphoryl lipid A (MPL, see U.S. Pat. Nos. 4,912,094 and 4,987,237) and it's derivatives and synthetic analogues and the CpG DNA motif and its derivatives and analogues.

The proportion of immunogen and adjuvant can be varied over a broad range so long as both are present in effective amounts. For example, aluminum hydroxide can be present in an amount of about 0.5% of the vaccine mixture ($Al_2O_3$ basis). Conveniently, the vaccines are formulated to contain a final concentration of immunogen in the range of from 0.2 to 200 mg/mL, preferably 5 to 50 mg/mL, most preferably 15 mg/mL.

The effectiveness of an adjuvant may be determined by measuring the amount of antibodies directed against an immunogenic agent resulting from administration of this agent in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Dosage and Administration of Vaccines

The vaccines are administered in a manner compatible with the dosage formulation, and in such amount as will be prophylactically and/or therapeutically effective. A prophylactic vaccine is one which prevents disease. The quantity to be administered, may be, for example, 5 µg to 250 µg of antigen per dose, depends on the subject to be treated, capacity of the subject's immune system to synthesize antibodies, the degree of protection desired and the nature of the antigen. A suitable range is from about 20 µg to about 40 µg per dose.

A suitable dose size is about 0.5 mL. Accordingly, a dose for intramuscular injection, for example, may comprise 0.5 mL containing 20 µg of immunogen in admixture with 0.5% adjuvant.

Precise amounts of active ingredient required to be administered may depend on the judgement of the practitioner and may be peculiar to each subject.

The vaccine may be given in a single dose schedule, or in a multiple dose schedule. A multiple dose schedule is one in which a primary course of vaccination may be with 1-10 separate doses, followed by other doses given at subsequent time intervals required to maintain and or reinforce the immune response, for example, at 2 to 4 weeks after the first dose, and if needed, a subsequent dose(s) after several months. The dosage regimen will also, at least in part, be determined by the need of the individual and be dependent upon the judgement of the practitioner.

In addition, the vaccine containing the antigen(s) may be administered in conjunction with other immunoregulatory agents, for example, immunoglobulins.

Preparation of Antibodies Using the Compositions of the Invention

Compositions according to the invention may be used directly as immunogens to generate antisera and monoclonal antibodies. The invention thus provides a method for inducing antigen specific immunoglobulin production comprising the steps of:

(a) immunising a subject with a composition according to the present invention; and (b) recovering immunoglobulin specific for a region of the antigen of the composition from the serum of the subject.

The animals used for antibody production may be any animals normally employed for the purpose, particularly mammals. Especially indicated are mice, rats, guinea pigs and rabbits.

Immunisation is carried out according to established techniques (See ANTIBODIES, A LABORATORY MANNUAL by E. Harlow and D. Lane (Cold Spring Harbor, U.S.A., 1988). The purified composition (about 1 mg) was injected into a rabbit. A booster injection of 0.5 mg of the composition was made 4 weeks after the initial injection. Antibodies are isolated from rabbit serum and tested for reactivity. Antibodies capable of selective binding to the chosen antigen are obtained by this method.

More particularly, the composition of the present invention comprising the antigen can be used to produce antibodies, both polyclonal and monoclonal. If polyclonal antibodies are desired, a selected mammal (e.g., mouse, rabbit, goat, horse, etc.) is immunised. Serum from the immunised animal is collected and treated according to known procedures. If serum containing polyclonal antibodies to other antigens, the polyclonal antibodies can be purified by immunoaffinity chromatography. Techniques for producing and processing polyclonal antisera are known in the art.

Monoclonal antibodies directed against antigens used in the invention can also be readily produced by one skilled in the art. The general methodology for making monoclonal antibodies by hybridomas is well known Immortal antibody-producing cell lines can be created by cell fusion, and also by other techniques such as direct transformation of B lymphocytes with oncogenic DNA, or transfection with Epstein-Barr virus. Panels of monoclonal antibodies produced against antigens can be screened for various properties; i.e., for isotype and epitope affinity.

An alternative technique involves screening phage display libraries where, for example the phage express scFv fragments on the surface of their coat with a large variety of complementary determining regions (CDRs). This technique is well known in the art.

Antibodies, both monoclonal and polyclonal, which are directed against antigens are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the antigen of the infectious agent against which protection is desired.

Techniques for raising anti-idiotype antibodies are known in the art. These anti-idiotype antibodies may also be useful for treatment, as well as for an elucidation of the immunogenic regions of antigens.

For the purposes of this invention, the term "antibody", unless specified to the contrary, includes fragments of whole antibodies which retain their binding activity for a target antigen. Such fragments include Fv, F(ab') and F(ab')2 fragments, as well as single chain antibodies (scFv). Furthermore, the antibodies and fragments thereof may be humanised antibodies, for example as described in EP-A-239400.

The invention will be described with reference to the following Example which is intended to be illustrative only and not limiting.

EXAMPLE 1

IgE, IgA and IgG1, IgG2A and IgG2B Response to Ovalbumin+Di-Oleoyl Phosphatidyl Serine, Lyso-Oleoyl Phosphatidyl Serine or Stearoyl($X_1$)—Arachidonoyl($X_2$) Phosphatidyl Serine Administration Rats were injected with vaccine compositions comprising the ovalbumin antigen with and without di-oleoyl phosphatidyl serine, lyso-oleoyl phosphatidyl serine or stearoyl($X_1$)-arachidonoyl($X_2$) phosphatidyl serine and the concentrations of IgE, IgA and IgG are compared.

The animals were acclimatised for a period of 5 days prior to dosing. During the acclimatisation period animals were observed twice daily during the working week and once on each day during the weekend to evaluate the health status of the animals. Rats were then allocated to the following dose groups using computer-generated random order numbers.

TABLE 1

| GROUP NO. | ANIMAL NO. | DAY 0 IMMUNISATION | DAY 21 IMMUNISATION | DAY 42 IMMUNISATION |
|---|---|---|---|---|
| 1 (n = 6) | 1-6 | 20 μg Ova + Alh | Nil | Nil |
| 2 (n = 6) | 7-12 | 20 μg Ova + Alh | 20 μg Ova | 20 μg Ova |
| 3 (n = 6) | 13-18 | 20 μg Ova + Alh | 20 μg Ova + 250 ug VT001 | 20 μg Ova + 250 ug VT001 |
| 4 (n = 6) | 19-24 | 20 μg Ova + Alh | 20 μg Ova + 50 ug VT001 | 20 μg Ova + 50 ug VT001 |
| 5 (n = 6) | 25-30 | 20 μg Ova + Alh | 20 μg Ova + 250 ug VT002 | 20 μg Ova + 250 ug VT002 |
| 5 (n = 6) | 31-36 | 20 μg Ova + Alh | 20 μg Ova + 50 ug VT002 | 20 μg Ova + 50 mg VT002 |
| 7 (n = 6) | 37-42 | 20 μg Ova + Alh | 20 μg Ova + 250 ug VT003 | 20 μg Ova + 250 ug VT003 |
| 8 (n = 6) | 43-48 | 20 μg Ova + Alh | 20 μg Ova + 50 ug VT003 | 20 μg Ova + 50 ug VT003 |

Ova = ovalbumin
Alh = Alhydrogel
VT001 = Dioleoyl phosphatidyl serine
VT002 = Lyso oleoyl phosphatidyl serine
VT003 = Stearoyl arachadonoyl phosphatidyl serine On day 0, 20 μg of ovalbumin (OA) in phosphate buffered saline (PBS) with alhydrogel (AHG) adjuvant in a final volume of 0.5 mL was administered.

On days 21 and 42, 20 μg of ovalbumin (OA) in phosphate buffered saline (PBS) with the relevant test compound in a final volume of 0.5 ml was administered.

In each case, 0.5 mL of inoculum was injected subcutaneously into the scruff of the neck.

On Day 0 a pre-inoculation blood sample was taken. A blood sample was also taken from each animal on Days 15, 22, 29, 36, 43, 50, 57 and 64.

Serum was prepared by centrifugation of the blood sample at 2,500 rpm for 10 minutes and frozen at −20° C. The samples were then analysed by ELISA to establish the concentration of IgE, IgA and IgG1, IgG2a and IgG2b.

ELISA

The purpose of an ELISA is to determine whether a particular protein is present in a sample and then enables quantification of how much is present. By coating the bottom of wells with ovalbumin (OVA) it is possible to bind anti-OVA specific antibodies. To detect only anti-OVA IgA antibodies anti-rat IgA conjugated to HRP was used as a secondary antibody. Quantification of specific antibodies in the rat sera samples was performed using antibody titrations. The data was reported as endpoint titers. Endpoint titers are defined as the last serum dilution giving an optical density value equal to twice the background optical density for the ELISA plate (buffer).

The results are presented below:

TABLE 2

| POOLED GROUP No. | IgE DAY No. | | | | | | | | |
|---|---|---|---|---|---|---|---|---|---|
| | 1 | 15 | 22 | 29 | 36 | 43 | 50 | 57 | 64 |
| 1 | 0 | 0 | 0 | 0 | 20 | 40 | 0 | 0 | 0 |
| 2 | 0 | 0 | 0 | 0 | 20 | 20 | 640 | 80 | 40 |
| 3 | 0 | 0 | 0 | 40 | 40 | 80 | 1280 | 160 | 40 |
| 4 | 0 | 0 | 0 | 0 | 40 | 0 | 1280 | 160 | 0 |
| 5 | 0 | 0 | 0 | 0 | 20 | 40 | 640 | 160 | 160 |
| 6 | 0 | 0 | 0 | 80 | 40 | 80 | 1280 | 320 | 160 |
| 7 | 0 | 0 | 0 | 0 | 0 | 0 | 80 | 40 | 20 |
| 8 | 0 | 0 | 0 | 0 | 0 | 0 | 320 | 80 | 40 |

TABLE 3

| POOLED GROUP No. | IgA DAY No. | | | | | | | | |
|---|---|---|---|---|---|---|---|---|---|
| | 1 | 15 | 22 | 29 | 36 | 43 | 50 | 57 | 64 |
| 1 | 0 | 0 | 0 | 0 | 160 | 160 | 80 | 160 | 160 |
| 2 | 0 | 0 | 0 | 80 | 320 | 320 | 640 | 1280 | 640 |

TABLE 3-continued

| POOLED GROUP | IgA DAY No. | | | | | | | | |
|---|---|---|---|---|---|---|---|---|---|
| No. | 1 | 15 | 22 | 29 | 36 | 43 | 50 | 57 | 64 |
| 3 | 0 | 0 | 0 | 320 | 640 | 640 | 1280 | 1280 | 640 |
| 4 | 0 | 0 | 0 | 320 | 640 | 320 | 1280 | 1280 | 640 |
| 5 | 0 | 0 | 0 | 0 | 80 | 160 | 1280 | 1280 | 1280 |
| 6 | 0 | 0 | 0 | 0 | 160 | 320 | 2560 | 1280 | 2560 |
| 7 | 0 | 0 | 0 | 40 | 160 | 320 | 640 | 640 | 1280 |
| 8 | 0 | 0 | 0 | 40 | 640 | 640 | 1280 | 640 | 640 |

TABLE 4

| POOLED GROUP No. | IgG1 DAY No. | | | | | | | | |
|---|---|---|---|---|---|---|---|---|---|
| | 1 | 15 | 22 | 29 | 36 | 43 | 50 | 57 | 64 |
| 1 | 0 | 640 | 5120 | 5120 | 10240 | 2560 | 2560 | 2560 | 5120 |
| 2 | 0 | 320 | 2560 | 10240 | 20480 | 10240 | 10240 | 10240 | 20480 |
| 3 | 0 | 160 | 2560 | 20480 | 40960 | 10240 | 10240 | 40960 | 20480 |
| 4 | 0 | 160 | 2560 | 40960 | 20480 | 10240 | 20480 | 40960 | 20480 |
| 5 | 0 | 640 | 2560 | 5120 | 20480 | 10240 | 20480 | 40960 | 40960 |
| 6 | 0 | 320 | 2560 | 10240 | 20480 | 20480 | 40960 | 40960 | 40960 |
| 7 | 0 | 320 | 2560 | 20480 | 20480 | 10240 | 10240 | 10240 | 20480 |
| 8 | 0 | 320 | 2560 | 20480 | 20480 | 20480 | 20480 | 10240 | 40960 |

TABLE 5

| POOLED GROUP No. | IgG2a DAY No. | | | | | | | | |
|---|---|---|---|---|---|---|---|---|---|
| | 1 | 15 | 22 | 29 | 36 | 43 | 50 | 57 | 64 |
| 1 | 0 | 640 | 1280 | 1280 | 1280 | 2560 | 5120 | 2560 | 2560 |
| 2 | 0 | 640 | 1280 | 1280 | 2560 | 5120 | 20480 | 20480 | 10240 |
| 3 | 0 | 640 | 1280 | 2560 | 5120 | 10240 | 40960 | 40960 | 20480 |
| 4 | 0 | 40 | 2560 | 5120 | 10240 | 10240 | 40960 | 40960 | 20480 |
| 5 | 0 | 80 | 640 | 1280 | 2560 | 2560 | 20480 | 20480 | 20480 |
| 6 | 0 | 40 | 1280 | 2560 | 5120 | 5120 | 20480 | 20480 | 20480 |
| 7 | 0 | 40 | 1280 | 2560 | 5120 | 5120 | 20480 | 10240 | 20480 |
| 8 | 0 | 40 | 1280 | 2560 | 10240 | 10240 | 20480 | 10240 | 20480 |

TABLE 6

| POOLED GROUP No. | IgG2b DAY No. | | | | | | | | |
|---|---|---|---|---|---|---|---|---|---|
| | 1 | 15 | 22 | 29 | 36 | 43 | 50 | 57 | 64 |
| 1 | 0 | 320 | 640 | 640 | 320 | 1280 | 640 | 1280 | 2560 |
| 2 | 0 | 1280 | 640 | 640 | 640 | 640 | 640 | 5120 | 5120 |
| 3 | 0 | 320 | 640 | 640 | 2560 | 1280 | 1280 | 5120 | 5120 |
| 4 | 0 | 160 | 320 | 160 | 160 | 160 | 2560 | 5120 | 5120 |
| 5 | 0 | 40 | 80 | 40 | 320 | 640 | 5120 | 5120 | 2560 |
| 6 | 0 | 0 | 0 | 160 | 320 | 640 | 640 | 2560 | 1280 |
| 7 | 0 | 40 | 80 | 80 | 640 | 1280 | 320 | 1280 | 1280 |
| 8 | 0 | 40 | 320 | 40 | 640 | 320 | 160 | 640 | 640 |

EXAMPLE 2

Inhibition of Pro—Inflammatory Cytolkine Release

Co-cultures of peripheral blood mononuclear cells (PBMC) expressing CD14, TLR2 and TLR4 are layered on airways smooth muscle cells (ASMC), which are unresponsive to Toll-like receptor (TLR) agonists but do respond to pro-inflammatory cytokines, according to the method described by Morris et. al., AMERICAN JOURNAL OF CRITICAL CARE 171:814-822, (2005). The co-cultures are challenged with lipopolysaccharide (LPS) and generate pro-inflammatory cytokines including IL6 and IL8. The direct effect of the phosphatidyl serine derivatives (PS) on the release of pro and anti-inflammatory cytokines from the two cell types and the co-culture is measured. A number of cultures and co-cultures are exposed to various concentrations of PS (including di-oleoyl, lyso oleoyl or steroyl arachidonyl derivatives as used in Example 1) before, or after the addition of LPS or at the same time as the LPS challenge and the resulting levels of pro and anti inflammatory cytokines are measured.

The results of measurement of cytokines released indicated that certain PS molecules have the ability to modulate the effects of LPS in such a way that the compounds will have clinical use in control of various human inflammatory lesions

EXAMPLE 3

Inhibition of Histamine Release from Mast Cells and Basophils

Compositions comprising phosphatidyl serine receptor ligands may reduce the inflammatory response seen in asthma and have utility in treating allergic disease, such as controlling inflammation involving histamine release at various anatomical sites caused by allergens and other mediators.

Anti human IgE-induced release of histamine from primary human lung mast cells (HLMC) by phosphatidyl serines is measured. The HLMC is taken from normal human lung washings and incubated with phosphatidyl serine derivatives (including di-oleoyl, lyso oleoyl or steroyl arachidonyl derivatives as used in experiment 1) alone, Anti IgE or pre-incubated with phosphatidyl serine before the addition of the anti IgE. Histamine released into the supernatant is measured.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

We claim:

1. A method of modulating an immune response to an antigen or allergen in a human or animal subject, comprising administering to the subject a stearoyl-arachidonoyl phosphatidylserine, wherein the stearoyl-arachidonoyl phosphatidylserine is administered to the subject separately, sequentially, or simultaneously with the antigen or allergen.

2. A method of modulating an immune response to an antigen or allergen in a human or animal subject, comprising administering to the subject a stearoyl-arachidonoyl phosphatidylserine, wherein the stearoyl-arachidonoyl phosphatidylserine is administered to the subject prior to, simultaneously with, or after encounter with the antigen or allergen.

3. The method of claim 2, wherein the stearoyl-arachidonoyl phosphatidylserine is administered to the subject prior to or after exposure of the subject to the antigen or allergen.

4. The method of claim 2, wherein the immune response being modulated is an immune response to a bacterial infection, a viral infection, cancer, or is an allergic reaction or an immune hypersensitivity reaction.

5. The method of claim 4, wherein the immune hypersensitivity reaction is a pre-existing disorder.

6. The method of claim 4, wherein the immune hypersensitivity reaction is a Type 1 hypersensitivity reaction.

7. The method of claim 1 or 2, wherein the antigen is derived from a bacterium, a virus, or a neoplasm.

8. The method of claim 1 or 2, wherein the antigen or allergen is a polypeptide or a vector comprising a polynucleotide encoding an antigenic polypeptide and operably linked to a regulatory sequence permitting expression of the polynucleotide.

9. The method of claim 2, wherein the immune response being modulated is a result of asthma, hay fever, systemic anaphylaxis, or contact dermatitis.

10. The method of claim 1 or 2 wherein the modulation of the immune response comprises reducing levels of allergen or antigen specific IgE antibodies.

11. The method of claim 1 or 2, wherein the immune response being modulated is an immune response to an allergic reaction or an immune hypersensitivity reaction.

* * * * *